United States Patent [19]

Aksamit

[11] Patent Number: 4,970,162
[45] Date of Patent: Nov. 13, 1990

[54] HUMAN-MOUSE HYBRID CELL LINE EXPRESSING MONOCYTE-MACROPHAGE PROPERTIES

[75] Inventor: Robert R. Aksamit, Rockville, Md.

[73] Assignee: The United States of America as represented by the Department of Health and Human Services, Washington, D.C.

[21] Appl. No.: 797,440

[22] Filed: Nov. 13, 1985

[51] Int. Cl.$^5$ .............................................. C12N 5/28
[52] U.S. Cl. ............................ 435/240.26; 435/172.2; 435/948; 435/70.21; 935/95; 935/96; 935/106; 935/108; 935/110; 935/111
[58] Field of Search ............. 435/240.26, 172.2, 70.21, 435/948; 935/95, 96, 106, 108, 110, 111

[56] References Cited

PUBLICATIONS

Aksamit, R. R. et al., "Chemotaxis by Mouse Macrophage Cell Lines", *J. Immunol.*, 126(6): 2194–2199, Jun., 1981.

Yamamoto, S. et al., "Macrophage-Like Chemotactic Hybridomas Active for Various Chemotactic Factors", *Biomedical Research*, 5(2): 91–100, 1984.

Harvath, L. et al., "Oxidized N-Formylmethionyl-Leucyl-Phenylalanine: Effect on the Activation of Human Monocyte and Neutrophil Chemotaxis and Superoxide Production", *J. Immunol.*, 133(3): 1471–1476, Sep., 1984.

Backlund et al., Proc. Natl. Acad. Sci. USA, 82:2637–41 (1985).

Yamamoto et al., Immunogenetics, 19:519–526 (1984).

Aksamit, FASEB Abstract, Apr. 1985.

Primary Examiner—Margaret Moskowitz
Assistant Examiner—Kay E. Cheney

[57] ABSTRACT

Human leukocytes, which contain monocytes and neutrophils that exhibit chemotaxis to N-formylmethionine-leucine-phenylalanine (FMLP), were fused with the mouse macrophage RAW264-TG3 cell line which exhibits chemotaxis to endotoxin-activated mouse serum (EAMS) but not to FMLP. From such fusions twelve cell lines were isolated, all of which migrated to EAMS. Four of the cell lines also exhibited chemotaxis to FMLP, and of these cell lines only one, WBC264-9, retained the capacity to migrate to FMLP after culture for 20 or more passages. WBC264-9 exhibits chemotaxis to FMLP and provides a novel system to investigate attractant-specific biochemical reactions necessary for chemotaxis.

2 Claims, 5 Drawing Sheets

100μm 1 2 3 4 5 6 7

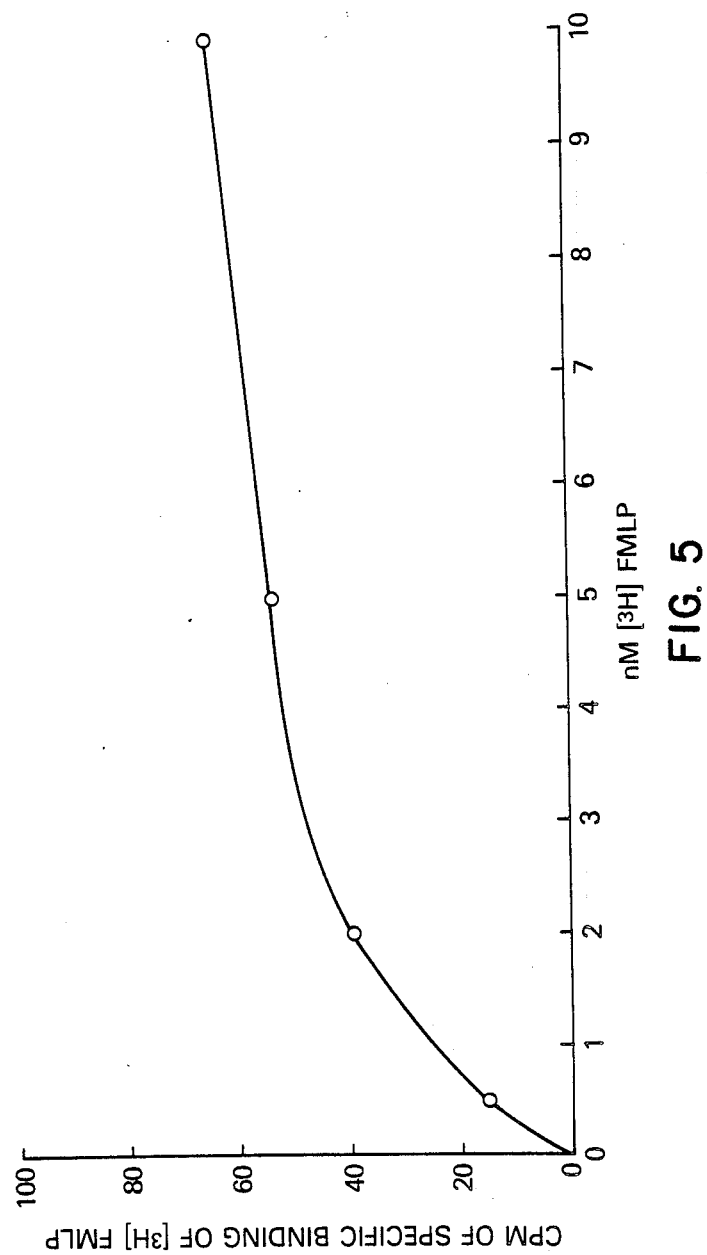

HUMAN-MOUSE HYBRID CELL LINE EXPRESSING MONOCYTE-MACROPHAGE PROPERTIES

BACKGROUND OF THE INVENTION

1. Technical Field

The present invention is related to a novel hybrid cell line. More particularly, the present invention is related to the production of a human-mouse hybrid cell line having monocyte-macrophage properties and capable of stably expressing attractant-specific biochemical reactions necessary for chemotaxis to certain peptide probes.

2. State of the Art

The use of advanced genetic and biochemical techniques has led to a fairly detailed understanding of the bacterial sensory mechanism. However, progress on the biochemical mechanism of mammalian cell chemotaxis has been limited primarily due to the unavailability of suitable experimental probes. The evaluation of the chemotactic behavior of cells treated with various compounds that result in decreased methylation is one approach that has been applied to both bacteria and mammalian cells. These studies indicate that methylation reactions may be involved in chemotaxis in both bacteria and mammalian cells.

The observation that N-formyl peptides are attractants for human neutrophils and monocytes suggested that this peptide may serve as a probe with which to study detailed binding of an attractant to a mammalian cell receptor. Several studies of the binding of N-formyl peptides to cells or membranes have indicated that the receptor may exist in more than one affinity state and that the binding can be affected by guanine nucleotides. These characteristics are reminiscent of the regulation of adenylate cyclase by guanine nucleotide binding proteins and are indicative that similar regulatory proteins may be involved in chemotaxis. The possible involvement of a guanine nucleotide binding protein in chemotaxis is supported by the observation that pertussis toxin is a potent inhibitor of macrophage chemotaxis.

Mouse macrophage cell line RAW264 has been used as a model system to evaluate biochemical reactions critical to mammalian cell chemotaxis. Inhibitor studies have shown that one or more methylation reactions are required for chemotaxis of RAW264 cells. A comparison of the metabolic alterations that occur upon treatment with the inhibitors and the effects produced on chemotactic activity led to the conclusion that methylation of phosphatidylethanolamine, previously thought to be involved in the transduction of the chemotactic signal, is not required for RAW264 chemotaxis.

The advantages of the RAW264 macrophage cell line as a model chemotaxis system relate to the ease with which the cells can be cultured and manipulated for chemotactic and biochemical assays and for the introduction of genetic changes. However, a limitation of the RAW264 cell line has been the lack of chemically defined attractants. The two attractants that have been described for RAW264 cells are endotoxin-activated mouse serum and lymphocyte-derived chemotaxis factor, a culture supernatant from mitogen-stimulated leukocytes. Both of these attractants are complex molecular mixtures with multiple biological activities. On the other hand, N-formylmethionine-leucine-phenylalanine (FMLP), a tripeptide attractant for leukocytes from humans and several animal species, is not an attractant for the mouse RAW264 cells. One way to overcome the problems imposed by the limited attractant specificity of the RAW264 cell line was to derive a cell line by fusion of thioguanine-resistant RAW264 cells with human leukocytes.

SUMMARY OF THE INVENTION

It is, therefore, an object of the present invention to provide a stable human-mouse hybrid cell line capable of expressing monocyte-macrophage properties and a method of producing the same.

It is a further object of the present invention to provide a human-mouse hybrid cell line that stably expresses chemotaxis to N-formylmethionine-leucine-phenylalanine (FMLP) and a method of producing the same.

Other objects and advantages would become apparent as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 5 shows specific binding of [$^3$H]FMLP to WBC264-9C membranes.

DETAILED DESCRIPTION OF INVENTION

Figure 1:
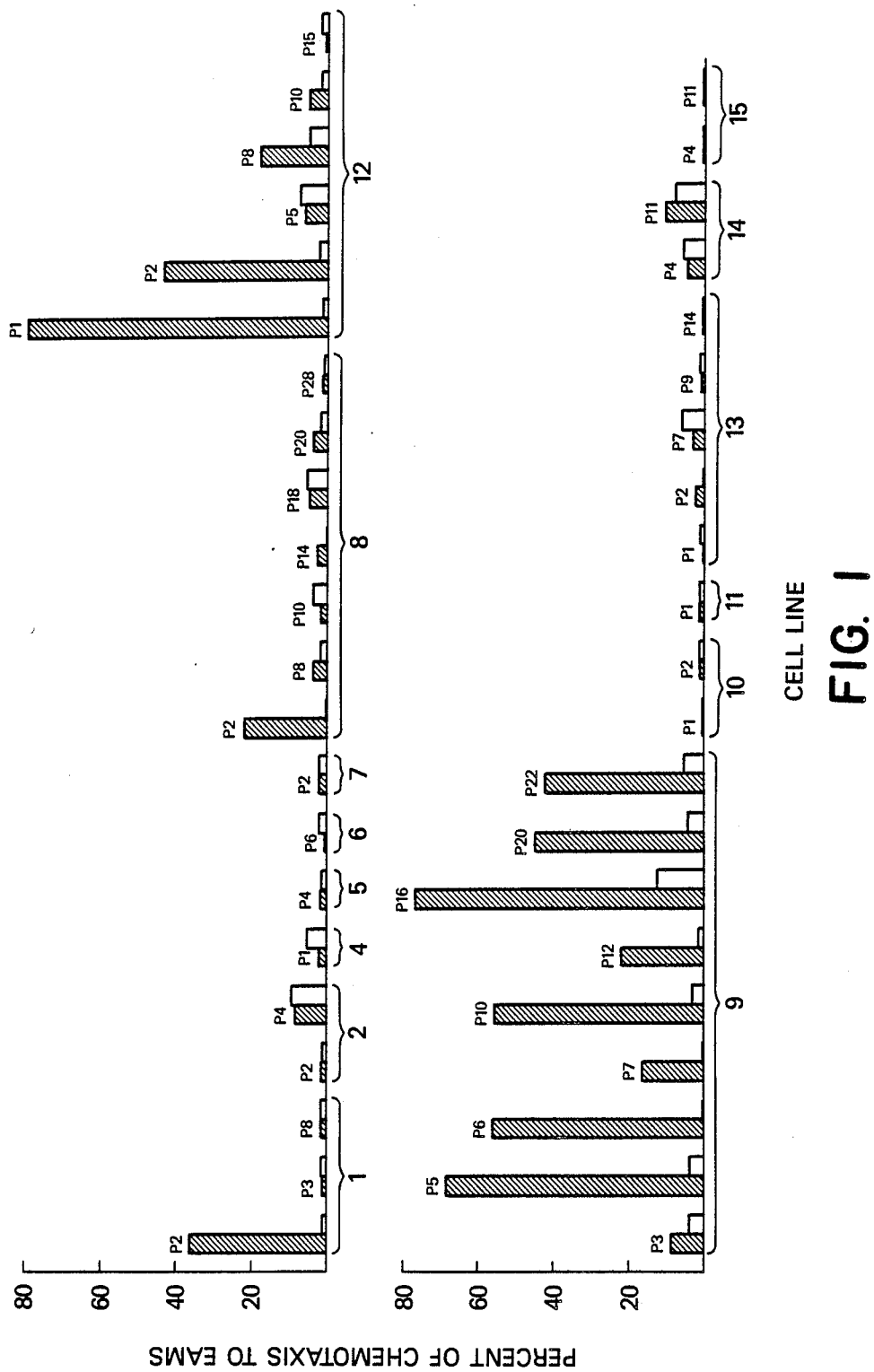
FIG. 1 demonstrates chemotaxis by hybrid cell lines. Chemotaxis to 30 nM FMLP was measured for twelve different cell lines at several different passages. Passage number is shown above the slashed bars. All cell lines migrated to a 1:200 dilution of EAMS, and migration to either FMLP (slashed bars) or medium (open bars) is expressed as a percentage of the EAMS response.

The above objects and advantages of the present invention are achieved by a stable human-mouse hybrid cell line having the identifying characteristics of ATCC HB8902 and being capable of expressing chemotaxis to FMLP.

Although any similar or equivalent methods and materials can be used in the practice of the present invention or for the tests described herein, the preferred materials and methods are now described. All publications mentioned hereunder are incorporated herein by reference.

The term "stable" or "stably expressing" as used herein is defined to mean that the cell line is capable of retaining sustained, normal growth through several passages, at least 70, in culture without loss or change of its essential phenotypic and biochemical monocyte-macrophage properties.

The term "attractant" as used herein means a substance that elicits directional movement of cells.

The term "chemotaxis" as used herein means directional movement of cells in response to a chemical gradient.

Preparation of Hybrids

Donor cells for cell fusions were normal human leukocytes isolated from 50 ml of heparinized blood by conventional dextran sedimentation. Three ml of 5% dextran solution (Clinical Grade Dextran, average molecular weight 170,000, Sigma Chemical Co.) were added per 10 ml of blood, and, after sedimentation at 1 $\times$g for 40 min at room temperature (about 23° $-300$° C.) as much as possible of the leukocyte-rich layer above the red cell pellet was removed. The cells were diluted to 50 ml with Hanks balanced salt solution (GIBCO Laboratories, Grand Island, N.Y.) without Ca++, Mg++ and phenol red at 4° C., and the cell suspension was centrifuged at 150 $\times$g for 10 min. The cell pellet was washed twice in Hanks balanced salt solution without Ca++, Mg++ and phenol red at 4° C., and resuspended in the same balanced salt solution.

RAW264-TG3 were the recipient cells for the fusion and were obtained from a clone of RAW264 cells (ATCC TIB71) cultured in 50 $\mu$g/ml of 6-thioguanine. The RAW264 and RAW264-TG3 cell lines were grown in Eagle modified minimum essential medium (Flow Laboratories, McLean, Va.), MEM, containing 10% heat-inactivated fetal calf serum, 100 IU/ml of penicillin and 100 $\mu$g/ml of streptomycin. The hybrid cell lines were grown in the same medium containing $1 \times 10^{-4}$ M hypoxanthine, $4 \times 10^{-7}$ M aminopterin and $2 \times 10^{-5}$ M thymidine (HAT). Cells were scraped from flasks and were split twice a week as described by Aksamit, et al., J. Immunol. 126:2194 (1981).

Assays for hypoxanthine-guanine phosphoribosyl-transferase (HPRT) activity performed by the method of Long et al., Biochem. Genetics. 9:283, (1973) indicated that the RAW264-TG3 cell line contained $<0.1\%$ of the enzyme activity found in the RAW264 cell line. The chemotactic response of RAW264-TG3 to endotoxin-activated mouse serum (EAMS) was the same as that of the RAW264 cells. The RAW264-TG3 cell line exhibiting the desired properties was maintained in culture and/or cryopreserved following standard procedures.

For fusion, RAW264-TG3 cells were pooled from seventeen 75-Cm$^2$ T-flasks, centrifuged, washed twice in MEM and resuspended in 40 ml of MEM. Fusion with human leukocytes was performed in suspension with 35% polyethylene glycol 1000 (BDH Chemical Ltd., Poole, England). To prepare the polyethylene glycol solution, 3.5 g of polyethylene glycol was melted in an autoclave, 6.5 ml of MEM was added to the cooled but liquid polyethylene glycol, and the pH was adjusted to 7.4. Human leukocytes ($1.87 \times 10^8$) and RAW264-TG3 ($1.87 \times 10^8$) were mixed, the cells centrifuged at 150 $\times$g for 10 min. and the supernatant was removed. The bottom of the tube was tapped to loosen the cell pellet, and the cells were gently suspended in 0.8 ml of the polyethylene glycol solution at 37° C. over a period of 1 min. After standing for an additional 1 min., the suspension was diluted by the dropwise addition of 1 ml of MEM for 1 min., followed by the addition of 20 ml of MEM during the next 5 min. The diluted suspension was centrifuged, the pellet was suspended in 50 ml of MEM containing 10% fetal calf serum, and 5 ml aliquots were added to each of ten 75-cm$^2$ T-flasks containing 20 ml of MEM with 10% heat-inactivated fetal calf serum. After about 12 to 16 hrs, the medium was replaced with HAT containing 10% heat-inactivated fetal calf serum. In most flasks a single clone appeared after 3–4 weeks and the clone was grown to a confluent cell layer. Cells at this stage were designated passage zero. Confluent cells were serially subcultured to obtain multiple passages as desired.

Chemotaxis

Chemotaxis by the cell lines was measured in a 48-well microchemotaxis chamber (Neuro Probe, Inc., Cabin John, Md.) with a 10 $\mu$m thick Nuclepore polycarbonate membrane coated with polyvinylpyrrolidone and containing 5 $\mu$m pores as described by Aksamit, et al., J. Immunol 126:2194 (1981). Upper wells contained 50,000 cells in MEM with 10% heat-inactivated fetal calf serum, and lower wells contained attractant in RPMI-1640 (GIBCO, Grand Island, N.Y.). Stock concentrations of FMLP were prepared in ethanol and diluted at least 1:100 in chemotaxis assays. EAMS was prepared as described by Aksamit et al., supra. Cells in the chemotaxis chamber were allowed to migrate for 4 hrs at 37° C. in an atmosphere of 5% $CO_2$ and 95% air. The top cells were wiped off the filter, and cells on the bottom were stained in Diff-Quik (Harleco, Gibbstown, N.J.). Chemotaxis was quantified by measurement of the optical density of the migrated cells.

Chromosome Number

Rapidly growing cell cultures were treated for 2–4 hrs with 0.1 $\mu$g/ml of colcemid, the cells were scraped into the medium, and were centrifuged at 150 $\times$g for 10 min. The supernatant was removed, leaving a small amount of the solution over the cell pellet. The tube was shaken to resuspend the cells, 10 to 15 ml of 0.075 M KCl was added dropwise while the tube was shaken, and the cell suspension was incubated at room temperature for approximately 20 min with periodic microscopic observations to monitor the degree of swelling. For each 5 ml of suspension two drops of freshly prepared fixative (absolute ethanol:glacial acetic acid, 3:1, v/v) were added while the tube was shaken. The suspension was centrifuged at 150 $\times$g for 5 min, the cell pellet was resuspended by shaking, 10–12 ml of fixative was added dropwise, and the suspension was incubated at room temperature for 10 min. The cells were centrifuged and again treated with fixative for 5 min. After centrifugation the pellet was suspended in enough fixative to give a slightly turbid solution and the suspension was dropped onto alcohol cleaned slides. The slides were air dried and stained with Giemsa. (Giemsa Stain Solution, Fisher Scientific Co.).

Acquisition of Human HPRT by Hybrid Cell Line

Vertical polyacrylamide slab gels were prepared by ammonium persulfate and TEMED (N,N,N',N'-Tetramethylethylenediamine, Bio-Rad Laboratories, Richmond, Cal.) catalyzed polymerization of a solution that contained 7.79% acrylamide, 0.21% bisacrylamide, 2.0% ampholytes (pH 5-7, LKB), 0.25% ampholytes (pH 3-10) and 0.25% ampholytes (pH 6-8). After polymerization the top of the gel was overlayed with 2% ampholytes (pH 5-7) and prefocused for 45 min at 400 volts. (Model 494 Isco Electrophoresis Power Supply Electrophoresis apparatus was made by NIMH Research Services but is similar to many models supplied commercially, e.g. Bio-Rad, Hoefer, Bethesda Research Lab). The upper electrolyte solution was 0.03M NaOH and the lower solution was 0.01M $H_3PO_4$. After prefocusing, the top of the gel was rinsed with 2% ampholytes (pH 5-7), overlayed with a solution of 2% ampholytes (pH 5-7) and 10% glycerol, and samples in a solution of 2% ampholytes (pH 5-7) and 20% glycerol were placed in wells. For the start of electrofocusing the voltage was 200 volts, and after 15 min the voltage was increased to 400 volts for the next 5 hours. The gels were then removed and stained for HPRT activity by the method of Tischfield et al., Anal. Biochem. 53:545 (1973).

Cell extracts of RAW264 and WBC264-9C were prepared from cell pellets that had been washed twice with Dulbecco's phosphate buffered saline (GIBCO, Grand Island, N.Y.) without $Ca++$ and $Mg++$. The cell pellets were suspended in approximately an equal volume of $H_2O$ and sonicated. Human red cells from a Ficoll-Hypague separation of blood from a normal donor were washed twice in Dulbecco's phosphate buffered saline without $Ca++$ and $Mg++$ and lysed by suspension in an equal volume of $H_2O$. Broken cell preparations were centrifuged for 5 min in an Eppendorf centrifuge (Model #5412, Brinkmann). The soluble cell extracts were diluted with 2% ampholytes (pH 5-7) and 20% glycerol and were placed in sample wells.

Determination of FMLP receptors

In order to demonstrate that the WBC264-9C cell line of the present invention expresses FMLP receptors, membranes were prepared from WBC264-9C cells by the procedure described by Backlund et al., PNAS 82, 2637 (1985). Total FMLP binding was measured by incubation of membranes with [$^3$H]FMLP and separation of the membrane-associated [$^3$H]FMLP by filtration. Each assay consisted of 10 $\mu$g of membranes and 0.5 to 10nM of [$^3$H]FMLP (specific activity 48.3 Ci/mmole, New England Nuclear) in a volume of 0.25 ml. Incubations were performed at room temperature for 30 min. A 0.2 ml aliquot of the membrane suspension was filtered on Whatman GF/C glass fiber filters (Whatman Ltd., Maidstone, England), previously washed with 5 ml of 2% bovine serum albumin (Fraction V, Boehringer Mannheim) in Dulbecco's phosphate buffered saline without $Mg++$ and $Ca++$ (GIBCO Laboratories, Grand Island, N.Y.). The filters were then again washed 3 times with 5ml each of Dulbecco's phosphate buffered saline without $Mg++$ and $Ca++$. After the filters were dried and placed in a scintillation vial about 10 ml of scintillation fluid was added, and the amount of radioactivity was determined. Nonspecific binding was determined by the amount of radioactivity bound to the membranes in the presence of 5 $\mu$M nonradioactive FMLP. Specific binding is total binding minus nonspecific binding. The data presented in FIG. 5 indicates that the dissociation constant for FMLP is $2 \times 10^{-9}$ M.

Characteristics of WBC-264-9C Hybrid Cell Line

Unlike human monocytes or neutrophils, mouse RAW264 cells do not exhibit chemotaxis to FMLP. To isolate a continuous cell line that migrates to FMLP, fourteen hybrid cell lines were isolated from fusions of human leukocytes with the mouse RAW264-TG3 cell line and were screened for the capacity to migrate toward either a 1:200 dilution of EAMS or 30 nM FMLP. All of the hybrid cell lines exhibited chemotaxis to EAMS; and the results summarized in FIG. 1 show that four cell lines, derived from clones 1, 8, 9 and 12, exhibited chemotaxis to FMLP. Chemotaxis of cell lines 1 and 8 to FMLP was detected only at the earliest passage tested, and migration of cell line 12 to FMLP decreased steadily over about 8 passages. In contrast, migration of cell line 9 (WBC264-9) continued to display a high level of chemotaxis to FMLP for 20 passages. Chemotaxis by the four cell lines to FMLP was always less than the response to EAMS, and the ratio of WBC264-9 chemotaxis to EAMS and FMLP appeared to vary randomly (FIG. 1). These findings are indicative that the response to EAMS and FMLP may be regulated independently.

Chemotaxis by WBC264-9 to FMLP was maintained after repeated cloning. WBC264-9 was grown for 28 passages, cloned, grown for another 20 passages and cloned again. The final cloned cell line, WBC264-9C, has been cultured for 70 passages (35 weeks) and the chemotactic response to FMLP throughout has been similar to that shown in FIG. 1. A deposit of the final WBC264-9C has been made at the American Type Culture Collection (ATCC) under accession No. HB8902 and shall be maintained in viable condition at the ATCC during the entire term of the issued patent and shall be available to any person or entity without restriction but consistent with the provisions of the law.

Figure 2:
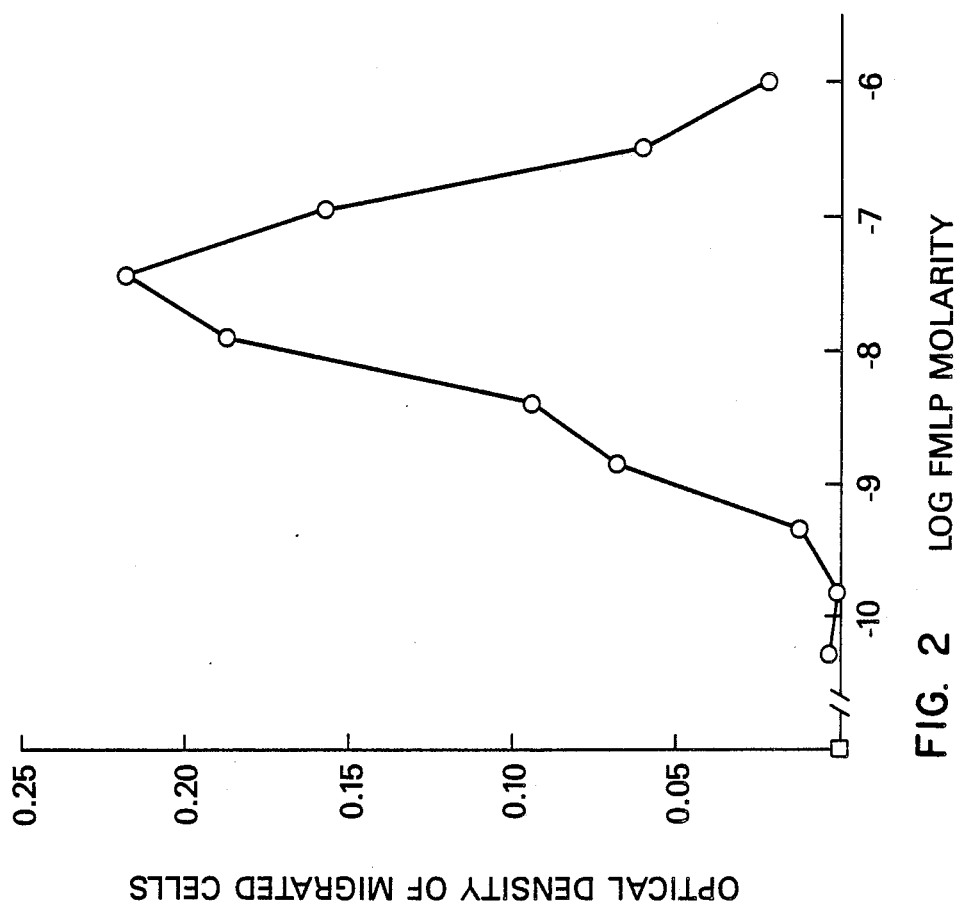
FIG. 2 demonstrates chemotaxis of WBC264-9 cells to different concentrations of FMLP. Chemotaxis was quantified by determination of the optical density of migrated cells after staining. Optical density is proportional to cell number.

The data in FIG. 1 clearly show that the WBC264-9 hybrid has permanently acquired the capacity to migrate to FMLP. The optimal chemotactic response of WBC264-9 to FMLP occurs at approximately $3 \times 10^{-8}$ M (FIG. 2), which is similar to the optimal chemotactic response of human monocytes as reported by Harvath, et al., J. Immunol. 133:1471 (1984).

Figure 3:
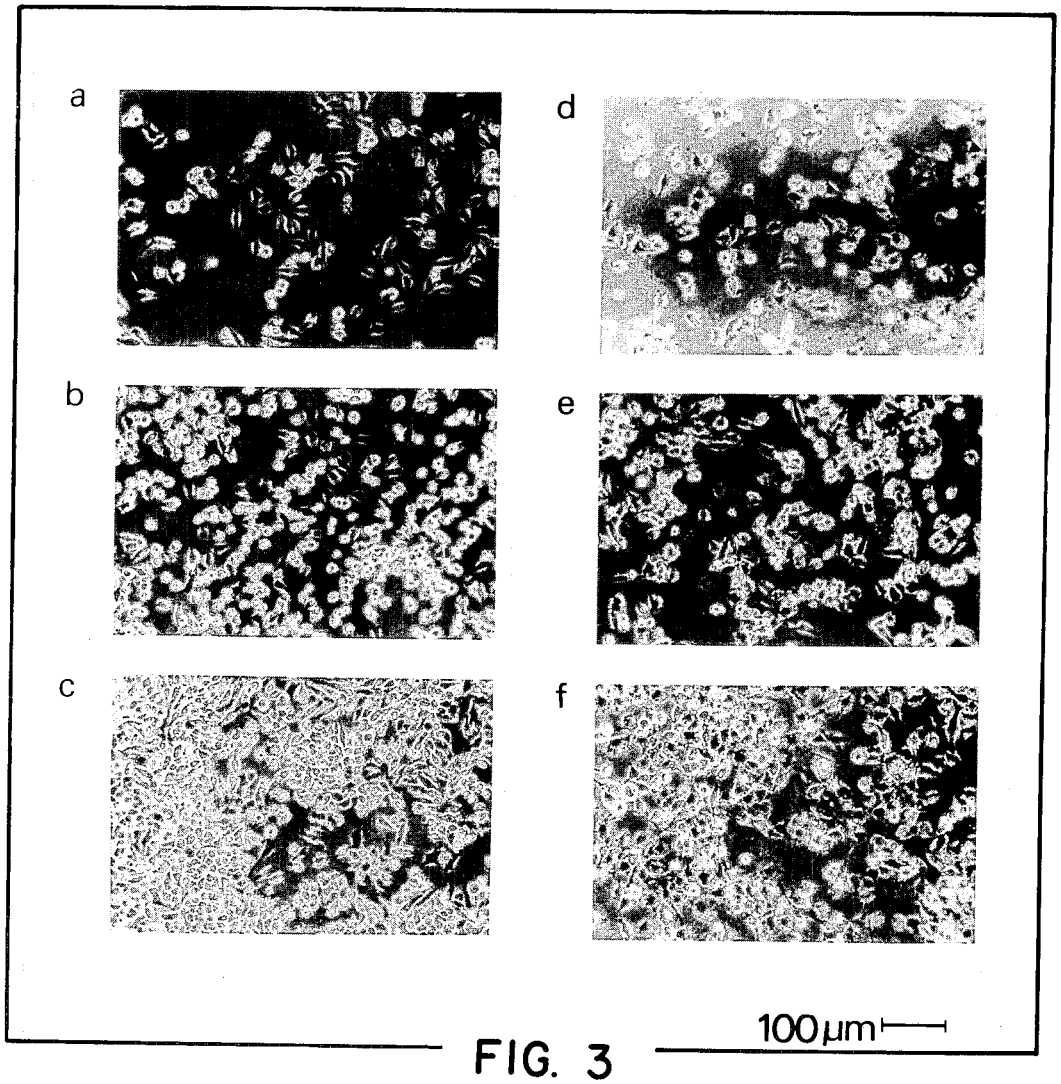
FIG. 3 shows phase-contrast photomicrographs of RAW264 (a, b and c) and WBC264 (d, e and f) cells. Cultures were seeded in flasks and photomicrographs were taken at various times. Both adherent and nonadherent cells are observed. The most dense cultures (c and f) are representative of 3-day cultures grown as described herein, infra.

In general, the morphology of the hybrid cell lines is similar to that of RAW264 cells. However, substantial differences are observed as shown in FIG. 3 for the WBC264-9 cell line. When compared to RAW264 cells, WBC-264-9 cells are slightly larger, adhere more tightly to plastic tissue culture flasks, and contain a larger number of endocytic vesicles when observed by phase contrast microscopy. Endocytic vesicles are especially apparent in WBC264-9 cells cultured in the same medium for 3 or 4 days (FIG. 3f).

The determination of the number of chromosomes in the cell lines at early passages indicated that many of the cell lines were derived from cell fusions (Table 1). RAW264-TG3 has 40 chromosomes (Table 1), the number expected for diploid mouse cells. The four cell lines derived from clones 1, 8, 9, and 12 and that migrated to FMLP contained more than 40 chromosomes, suggesting that these cell lines were hybrids. Cell lines derived from clones 2, 4, 6, 10, 11, and 15 had an average of 40 or less chromosomes. Therefore, on the basis of chromosome number, evidence for hybridization is not apparent for these cell lines. However, these cell lines presumably carry some human-derived genetic material that corrects for the HPRT deficiency of RAW264-

TG3, since the cell lines grow in HAT medium. Revertants of the parental TG-resistant cells would also be expected to grow in HAT medium, but the finding that no cell clones were obtained from either control fusions of RAW264-TG3 with itself or by direct selection in HAT medium of a number of RAW264-TG3 cells equal to that used for fusion argues against spontaneous revertants.

TABLE 1

Number of chromosomes of hybrid cell lines at early passages.

| Hybrid | Passage | Number of chromosomes Mean | Range | Number of Spreads |
|---|---|---|---|---|
| 1 | 5 | 97 | 86–113 | 6 |
| 2 | 7 | 37 | 35–40 | 16 |
| 4 | 6 | 39 | 34–42 | 10 |
| 6 | 2 | 40 | 38–41 | 15 |
| 8 | 5 | 73 | 62–84 | 5 |
| 9 | 6 | 64 | 36–81 | 10 |
| 10 | 4 | 36 | 20–43 | 23 |
| 11 | 4 | 40 | 37–42 | 16 |
| 12 | 4 | 95 | 85–98 | 14 |
| 13 | 4 | 71 | 43–84 | 7 |
| 14 | 6 | 126 | 119–132 | 4 |
| 15 | 9 | 39 | 38–40 | 12 |
| Human lymphocytes | / | 46 | 44–46 | 10 |
| RAW264-TG3 | 43 | 40 | 35–43 | 26 |
| RAW264 | +28 | 39 | 37–41 | 11 |

Figure 4:
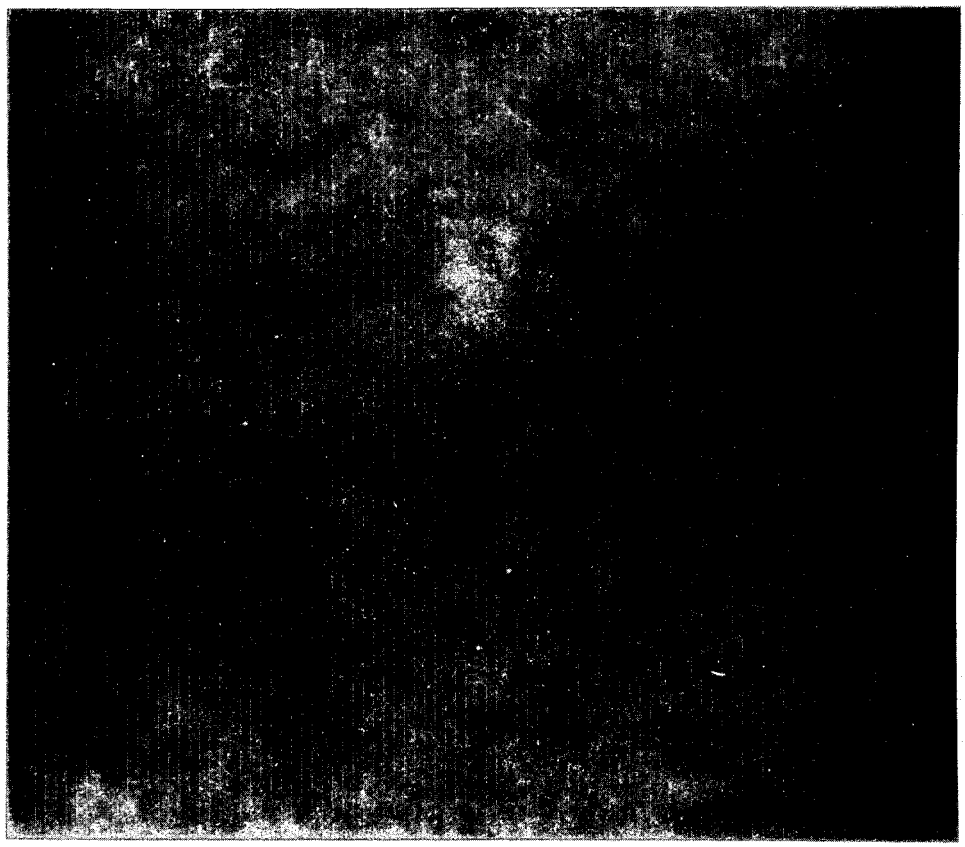
FIG. 4 shows HPRT activity stain of cell extracts after electrofusing in polyacrylamide gels. Cell extracts of human erythrocytes (2 $\mu$l, lane 1; 5 $\mu$l, lane 2), WBC264-9 cells (1 $\mu$, lane 3; 2 $\mu$l, lane 4; 5 $\mu$l, lane 5) and RAW264 cells (1 $\mu$l, lane 6; 2 $\mu$l, lane 7) were each applied in 20 $\mu$l, of 2% ampholytes and 20% glycerol. The pH is basic at the top of the figure and acid at the bottom.

Direct evidence was obtained in the case of WBC264-9C that this cell line expresses human HPRT. HPRT in cell extracts from human erythrocytes, hybrid WBC264-9 and mouse RAW264 were separated on polyacrylamide electrofocusing gels, and the gels were stained for enzyme activity. HPRT activity from mouse RAW264 cells was clearly separated from that of human erythrocytes. The broad band of HPRT activity from human erythrocytes is most likely due to 2 or 3 forms of the enzyme which have been observed previously upon electrofocusing (Davies, et al., FEBS Lett. 18:283, 1971; Der Kaloustian, et al., Biochem. Genet. 9:91, 1973). HPRT activity from WBC264-9 cells migrated close to the human HPRT activity that exhibited the most basic pH (FIG. 4).

The evidence presented herein supra, clearly demonstrates the isolation of a somatic cell hybrid possessing unique properties from a fusion between a thioguanine-resistant RAW264 macrophage cell line and human leukocytes. The hybrid, WBC264-9(C), exhibits chemotaxis to FMLP, a commercially available synthetic peptide as well as retains the desirable properties of the RAW264 cell line. Some human cell lines have been reported that can be induced to express chemotaxis to FMLP (Collins, et al., J. Exp. Med. 149:969, 1979; Pike, et al., J. Exp. Med. 152:31, 1980) and FMLP receptors (Pike, et al., J. Exp. Med. 152:31, 1980; Niedel, et al., Proc. Natl. Acad. Sci. USA 77:1000, 1980; Fontana, et al., Proc. Natl. Acad. Sci. USA 77:3664, 1980); however, it is noted that these induced cell lines are not capable of sustained growth in cell culture (Collins, et al., Proc. Natl. Acad. Sci. USA 75:2458, 1978). In contrast, the WBC264-9 cell line of the present invention continuously expresses FMLP receptors and is capable of normal sustained growth in culture (FIG. 5).

Of course, the availability of the WBC264-9C cell line of the present invention with its FMLP-specific biochemical reactions makes it possible to elucidate the mechanism involved in the transduction of the chemotactic signal in mammalian cells utilizing several approaches including genetic manipulation of these cells. Other utilities of this cell line e.g. in the study of inflammation in which macrophage chemotaxis is an integral component and the like ought to be obvious to the skilled artisan in this field.

It is understood that the examples and embodiments described herein are for illustrative purposes only and that various modifications or changes in light thereof will be suggested to persons of ordinary skill in the art and are to be included within the spirit and purview of this application and the scope of the appended claims.

I claim:

1. The stable human-mouse hybrid cell line having all of the identifying characteristics of the American type Culture Collection deposit accession number HB 8902, which grows in a medium that selects for the hypoxanthine-guanine phosphoribosyl-transferase phenotype possessed by the human cells but not by the mouse cells, wherein the human-mouse hybrid cell line is produced by a process comprising:

(a) fusing a thioguanine-resistant RAW 264 macrophage cell line, which is unable to grown in hypoxanthine-aminopterin-thymidine-containing medium, with human leukocytes, which exhibit chemotaxis to N-formylmethionine-leucine-phenylalanine;

(b) isolating hybrid cells that grow in said hypoxanthine-aminopterin-thymidine-containing medium; and (c) selecting from the hybrid cells those that also exhibit chemotaxis to N-formylmethionine-leucine-phenylalanine, wherein said chemotaxis to N-formylmethionine-leucine-phenylalanine is retained after subculturing the selected hybrid cells for at least 70 passages.

2. The human-mouse hybrid cell line that is deposited at the American Type Culture Collection and that has accession number HB 8902.

* * * * *